United States Patent [19]

Helmlinger

[11] Patent Number: 5,329,053
[45] Date of Patent: Jul. 12, 1994

[54] PROCESS FOR THE MANUFACTURE OF KNOWN ODORANTS

[75] Inventor: Daniel Helmlinger, Dübendorf, Switzerland

[73] Assignee: Givaudan-Roure Corporation, Clifton, N.J.

[21] Appl. No.: 111,694

[22] Filed: Aug. 25, 1993

[30] Foreign Application Priority Data

Sep. 3, 1992 [CH] Switzerland .................. 2770/92

[51] Int. Cl.[5] .................................................. C07C 33/14
[52] U.S. Cl. ................................ 568/824; 568/822; 568/823; 568/825
[58] Field of Search .............. 568/824, 825, 822, 823; 512/22; 252/522

[56] References Cited

U.S. PATENT DOCUMENTS

| | | | |
|---|---|---|---|
| 3,928,400 | 12/1973 | Olson et al. ................... | 568/824 |
| 4,095,038 | 6/1978 | Boguth et al. .................. | 568/824 |
| 4,271,324 | 6/1981 | Wilson et al. .................. | 568/824 |
| 4,503,240 | 3/1985 | Staiger et al. .................. | 568/819 |
| 4,613,710 | 9/1986 | Buchi et al. .................... | 568/819 |
| 4,623,750 | 11/1986 | Schulte-Elte et al. .......... | 568/822 |
| 4,626,381 | 2/1986 | Schulte-Elte et al. .......... | 252/522 |
| 4,633,011 | 12/1986 | Buchi et al. .................... | 560/119 |
| 4,677,233 | 6/1987 | Buchi et al. .................... | 549/819 |
| 5,077,417 | 12/1991 | Schulte-Elte et al. .......... | 549/458 |
| 5,155,238 | 10/1992 | Schulte-Elte et al. .......... | 549/398 |
| 5,155,239 | 10/1992 | Schulte-Elte et al. .......... | 549/398 |
| 5,250,512 | 10/1993 | Ohmoto et al. ................. | 512/22 |

FOREIGN PATENT DOCUMENTS

| | | |
|---|---|---|
| 155591 | 9/1985 | European Pat. Off. . |
| 165458 | 12/1985 | European Pat. Off. . |
| 170955 | 12/1986 | European Pat. Off. . |
| 403945 | 12/1990 | European Pat. Off. . |
| 3240054 | 5/1984 | Fed. Rep. of Germany . |

OTHER PUBLICATIONS

M. Fieser, et al., *Reagents for Organic Synthesis*, 1972, Wiley–Interscience (1971), pp. 260–261.
J. G. de Vries, et al, "Sodium Dithionite as a Reductant for Aldehydes and Ketones," Synthesis, 4, 1977, pp. 246–247.
European Search Report for Application No. 93,113,716.0 dated Dec. 12, 1993.
Derwent Abstract and Family Search of EP 165 458.
Derwent Abstract and Family Search of EP 170 955.
Derwent Abstract and Family Search of EP 403 945.
Derwent Abstract and Family Search of JP 90-258773.
Derwent Abstract and Family Search of JP 85-81164.
Derwent Abstract and Family Search of DE 3,240,054.

*Primary Examiner*—Werren B. Lone
*Attorney, Agent, or Firm*—George M. Gould; George W. Johnston

[57] ABSTRACT

A novel process is described for the manufacture of a mixture of 6-(2',6',6'-trimethyl-cyclohex-1'-en-1'-yl)-4-methyl-hex-3-en-1-ol and -4-en-1-ol (I) and, respectively, of a mixture of [3aα,5aβ,9aα,9bβ]-dodecahydro-3a,6,6,9a-tetramethylnaphtho[2,1-b]furan and [3aα,5aβ,9aα,9bα]-dodecahydro-3a,6,6,9a-tetramethylnaphtho[2,1-b]furan, in which E,E-6-(2',6',6'-trimethylcyclohex-1'-en-1'-yl)-4-methyl-hexa-2,4-dien-1-al is reduced either with (a) lithium aluminium hydride or with (b) sodium dithionite in the presence of sodium bicarbonate in aqueous solution and of a phase transfer catalyst or with (c) sodium borohydride or with (d) sodium bis(2-methoxyethoxy)aluminium dihydride and, when reduction agent (c) or (d) is used and optionally in the case when reduction agent (a) is used, the E,E-6-(2',6',6'-trimethyl-cyclohex-1'-en-1'-yl)-4-methyl-hexa-2,4-dien-1-ol which results as the intermediate is reduced to the desired 6-(2',6',6'-trimethyl-cyclohex-1'-en-1'-yl)-4-methyl-hex-3-en-1-ol and -4-en-1-ol using a reduction agent (a) or (b) and, if desired, the thus-obtained compounds I are converted in a known manner into a mixture of the aforementioned furans. These furans are suitable as odorants.

8 Claims, No Drawings

PROCESS FOR THE MANUFACTURE OF KNOWN ODORANTS

The present invention is concerned with a novel process for the manufacture of a mixture of 6-(2',6',6'-trimethyl-cyclohex-1'-en-1'-yl)-4-methyl-hex-3-en-1-ol and -4-en-1-ol (I), which is suitable as an intermediate for the production of odorants known, inter alia, under the trade names AMBROX DL ® and SYNAMBRAN ®. These odorants each consist essentially of a mixture of (-)-[3aα,5aβ,8aα,9bβ]-dodecahydro-3a,6,6,-9a-tetramethylnaphtho[2,1-b]furan and (±)-[3aα,5aβ,-9aα,9bα]-dodecahydro-3a,6,6,9a-tetramethylnaphtho[2,1-b]furan and are suitable replacements for the expensive optically active (−)-[3aR-(3aα, 5aβ, 9aα,9bβ)]-dodecahydro-3a,6,6,9a-tetramethylnaphtho[2,1-b]furan, which is commercially available under various trade names, namely AMBROX ® (Firmenich), AMBROXAN ® (Henkel), AMBERLYN ® (Quest), SYLVAMBER ® (BASF) and AMBROX-ID ® (Haarman & Reimer).

The present invention is also concerned with a process for the manufacture of the aforementioned mixture of [3aα,5aβ,9aα,9bβ]-dodecahydro-3a,6,6,9a-tetramethylnaphtho[2,1-b]furan and [3aα,5aβ,9aα,9bα]-dodecahydro-3a,6,6,9a-tetramethylnaphtho[2,1-b]furan.

Several processes for the manufacture of AMBROX ®, which start from sclareolid (or norambreinolid), i.e. [3aR-(3aα,5aβ,9aα,9bβ)]-decahydro-3a,6,6,9a-tetramethylnaphtho[2,1-b]furan-2(1H)one, are known. Sclareolid itself is obtained by oxidation, for example using chromic acid, of sclareol (Clary Sage oil) and sclareol in turn is obtained from the natural source Salvia sclarea by extraction. At present, however, the amount of sclareol which is commercially available is limited and the price can fluctuate enormously depending on the harvest of Salvia sclarea. A further disadvantage of this process is the oxidation step of sclareol to sclareolid with chromic acid which is problematic from the point of view of environmental protection.

Other hitherto known processes for the manufacture of dodecahydro-3a,6,6,9a-tetramethylnaphtho[2,1-b]furan usually proceed starting from the "key intermediate" β-ionone [see, for example, Japanese Patent Publication (Kokai) No. 81164/1985, Agric. Biol. Chem. 50 (6), 1475–1480 (1986), Chem. Lett. 1981, 757–760, Chem. Lett. 1983, 729–732, European Patent Publication No. 165 458, Helv. Chim. Acta 72, 996–1000 as well as European Patent Publication No. 170 955] or nerolidol [see German Offenlegungsschrift 3 240 054] which are frequently used in the chemical industry and which are commercially available. These processes are industrially unsatisfactory, because many (at least six) reaction steps are required.

There accordingly exists a need for an industrially realizable process for the manufacture of dodecahydro-3a,6,6,9a-tetramethylnaphtho]2,1-b]furan, which is not carried out via sclareol and accordingly which is not dependent on the availability of sclareol, but rather which starts from an intermediate (i.e. II) which is produced on a large scale and which is accordingly readily accessible and, moreover, which is more economical, efficient and environmentally friendly than the processes hitherto used. This is now possible by means of the process in accordance with the invention, since this starts directly from E,E-6-(2',6',6'-trimethyl-cyclohex-1'-en-1'-yl)-4-methyl-hexa-2,4-dien-1-al, i.e. the compound of the formula

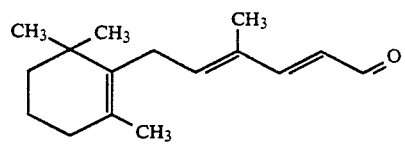

in E, E-form (see Carotenoids, Ed. Otto Isler, Birkhäuser editors Basel, 1971, pages 362–365), which is produced on a large scale and which is an important intermediate in the industrial synthesis of β-carotene, and requires only two or three steps (to the desired aforementioned odorant mixtures).

The process in accordance with the invention is a process for the manufacture of a mixture of 6-(2',6',6'-trimethyl-cyclohex-1'-en-1'-yl)-4-methyl-hex-3-en-1-ol and -4-en-1-ol, i.e. of compounds of the formula

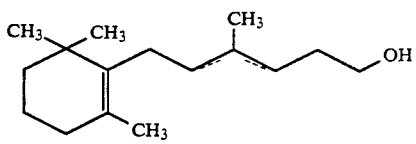

wherein one of the bonds ======== denotes a single bond and the other denotes a double bond,
or of a mixture of [3aα,5aβ,9aα,9bβ]-dodecahydro-3a,6,6,9a-tetramethylnaphtho[2,1-b]furan and [3aα,-5aβ,9aα,9bα]-dodecahydro-3a,6,6,9a-tetramethylnaphtho[2,1-b]furan and comprises reducing E,E-6-(2',6',6'-trimethyl-cyclohex-1'-en-1'-yl)-4-methyl-hexa-2,4-dien-1-al either with (a) lithium aluminium hydride or with (b) sodium dithionite in the presence of sodium bicarbonate in aqueous solution and of a phase transfer catalyst or with (c) sodium borohydride or with (d) sodium bis(2-methoxyethoxy)aluminium dihydride and, when the reducing agent (c) or (d) is used and optionally when the reducing agent (a) is used, the E,E-6-(2',6',6'-trimethyl-cyclohex-1'-en-1'-yl)-4-methyl-hexa-2,4-dien-1-ol, i.e. the compound of the formula

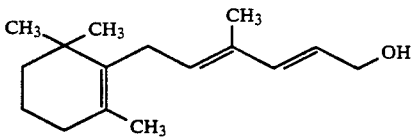

in E, E-form resulting as an intermediate is reduced further to the desired 6-(2',6',6'-trimethyl-cyclohex-1'-en-1'-yl)-4-methyl-hex-3-en-1-ol and -4-en-1-ol using a reducing agent (a) or (b), and, if desired, converting the thus-obtained compound of formula I is a known manner into a mixture of [3aα,5aβ,9aα, 9bβ]-dodecahydro-3a,6,6,9a-tetramethylnaphtho[2,1-b]furan and [3aα,-5aβ,9aα,9bα]-dodecahydro-3a,6,6,9a-tetramethylnaphtho[2,1-b]furan.

The usual abbreviated representation of the structural formulae which are used in chemistry, especially carotinoid chemistry, are used hereinbefore and hereinafter: aliphatic chains and cyclohexene rings are represented by single lines.

Geometric isomerism can occur by virtue of the presence of aliphatic C=C double bonds in certain compounds mentioned above and below, i.e. these compounds are present in the cis-(Z—) or the trans-(E—)

form, whereby in the polyenes any C=C double bond independently can be present in the one or the other form. Moreover, the possible presence of an asymmetric carbon atom means that the compounds can occur in optically isometric forms (+ or −). Unless otherwise indicated, the respective formulae and names embrace the isomeric forms which are possible as well as mixtures of isomers.

As will be evident from the above definition of the process in accordance with the invention, the respective first step comprises subjecting E,E-6-(2',6',6'-trimethyl-cyclohex-1'-en-1'-yl)-4-methyl-hexa-2,4-dien-1-al to a reduction. This reduction proceeds differently according to the reduction agent (a), (b), (c) or (d) which is used-and in the case of the reducing agent lithium aluminium hydride also the other reaction conditions. When lithium aluminium hydride (a) is used, there is primarily produced, depending on the reaction temperature, either the intermediate E,E-6-(2',6',6'-trimethyl-cyclohex-1'-en-1'-yl)-4-methyl-hexa-2,4-dien-1-ol (III; at relatively low temperatures) or immediately the 6-(2',6',6'-trimethyl-cyclohex-1'-en-1'-yl)-4-methyl-hex-3-en-1-ol and -4-en-1-ol (I; at relatively high temperatures). On the other hand, when sodium dithionite, (b) is used, i.e. (Rongalit ®), the compound I is always produced immediately and when sodium borohydride (c) or sodium bis(2-methoxyethoxy)-aluminium dihydride, e.g. Red-Al ®, Vitride ®, (d) is used, the compound III is always produced immediately. In those cases in which the compound III is the reduction product, this is subsequently converted into the desired compounds I using the reduction agent (a) (at relatively high temperatures) or (b). The course of the reaction can be represented schematically as follows:

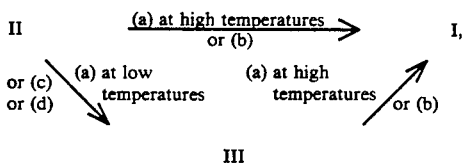

whereby the respective convenient reaction conditions are explained hereinafter.

In the case of the immediate conversion of the compound of formula II into the compounds of formula I by means of lithium aluminium hydride, this can conveniently be carried out by heating the compound of formula II in the presence of the said reduction agent in an ethereal solvent at temperatures between about 65° C. and about 165° C. Suitable ethereal solvents are those which have a boiling point from about 35° C. Aliphatic ethers, e.g. dimethoxyethane and diethylene glycol dimethyl ether, and cyclic ethers e.g. tetrahydrofuran, tetrahydropyran and dioxan, especially come into consideration. The reduction is preferably carried out at the reflux temperature of the respective reaction mixture. The reduction agent is conveniently used in a slight molar excess, i.e. up to about a ten percent molar excess. The safest procedure comprises the slow dropwise addition of a solution of the compound of formula II in the ethereal solution to a solution of lithium aluminium hydride in the same solvent at room temperature. The reaction is slightly exothermic. Subsequently, the reaction mixture is heated slowly to reflux temperature and held at reflux until the reaction has finished, which normally takes several hours. Conveniently, the dropwise addition and the heating are carried out while stirring the mixture continuously.

Where the conversion of the compound of formula II into the intermediate of formula III is performed using lithium aluminium hydride, then the reduction is effected in a lower boiling solvent at correspondingly lower temperatures. In this case, a relatively low boiling aliphatic ether such as, for example, diethyl ether and reaction temperatures of about room temperature to about 40° C. are conveniently used. Preferably, the reduction is carried out at the reflux temperature of the respective reaction mixture. Otherwise, the procedure described above in connection with the immediate conversion of the compound of formula II into the compounds of formula I using lithium aluminium hydride is conveniently used.

An immediate conversion of the compound of formula II into the compounds of formula I is also achieved using sodium dithionite in the presence of sodium bicarbonate in aqueous solution and of a phase transfer catalyst. In this case, in addition to water as the solvent, there can also be used an inert organic solvent, especially an alicyclic ether, e.g. tetrahydrofuran or dioxan, an aromatic hydrocarbon, e.g. benzene or toluene; or a lower aliphatic ester, e.g. ethyl acetate. The amount of sodium dithionite which is used is conveniently 1 to 4 equivalents based on the amount of the compound of formula II. The phase transfer catalyst which is used is especially a quaternary ammonium salt, e.g. triethylbenzylammonium chloride, tetrabutylammonium hydrogen sulphate or bromide, tributylbenzylammonium chloride, tricaprylmethylammonium chloride, trimethyl- or tributylhexadecylammonium chloride or trioctylmethylammonium chloride, or a phosphonium salt, e.g. hexadecyltributylphosphonium chloride, conveniently in an amount which corresponds to from 3 to 25 percent of the molar amount of starting material of formula II. Conveniently, 2 to 5 equivalents of sodium carbonate, which is also present in the reaction system, are conveniently used, again based on the amount of the compound of formula II. The reduction is conveniently carried out at the reflux temperature of the reaction mixture.

When sodium borohydride is used as the reduction agent, the reaction, which leads to the compound of formula III, is conveniently effected in an alcohol or aqueous alcohol as the solvent, with the alcohol being especially a lower aliphatic alcohol such as, for example, ethanol, propanol, isopropanol, n-butanol or tert.butanol. Moreover, the reaction is conveniently carried out at the reflux temperature of the reaction mixture. The amount of sodium borohydride which is used is conveniently from 0.25 to 1 equivalent based on the amount of starting material of formula II.

A conversion of the compound of formula II into the compound of formula III is also achieved when sodium bis(2-methoxyethoxy)aluminium dihydride is used as the reduction agent. In this case, the reduction is conveniently carried out in an organic solvent, especially an aromatic hydrocarbon, e.g. benzene or toluene, or a cyclic ether, e.g. tetrahydrofuran or dioxan, at the reflux temperature of the reaction mixture. The amount of reduction agent which is used is conveniently from 0.5 to 1 equivalent based on the amount of starting material.

In the three cases in which the intermediate of formula III is produced, this is in accordance with the invention converted into the compound of formula I using lithium aluminium hydride (at elevated temperatures, especially between about 65° C. and about 165° C.) or sodium dithionite as the reduction agent. The respective reaction conditions correspond in general to those which are described above in connection with the immediate conversion of the compound of formula II into the compounds of formula I using sodium aluminium hydride and, respectively, sodium dithionite.

The respective working up and isolation of the reduction product of formula III or I can be effected according to methods known per se.

Insofar as no planned synthesis for the isolation of pure isomers is carried out, the product can be obtained as a mixture of two or more isomers. This occurs in any event when the starting material of formula II is present as a mixture of isomers. Furthermore, the reduction product is normally obtained as a mixture of E- and Z-6-(2',6',6'-trimethyl-cyclohex-1'-en-1'-yl)-4-methyl-hex-3-en-1-ol as well as E- and/or Z-6-(2',6',6'-trimethylcyclohex-1'-en-1'-yl)-4-methyl-hex-4-en-1-ol, whereby as a rule the main part of the product of formula I consists of a mixture of E-and Z-6-(2',6',6'-trimethyl-cyclohex-1'-en-1'-yl)-4-methyl-hex-3-en-1-ol.

Where desired, the thus-manufactured isomers can be separated according to methods known per se, such as fractional crystallization or column chromatography. In practice this is, however, usually not necessary, as the reduction product is converted in a further reaction step into the desired odorant and the separation—where required—can be carried out after this conversion.

The conversion of the compounds of formula I obtained into the mixture of [3α, 5aβ, 9aα, 9bβ]-dodecahydro-3a,6,6,9a-tetramethylnaphtho[2,1-b]furan and [3aα,5aβ,9aα,9bα]-dodecahydro-3a,6,6,9a-tetramethylnaphtho[2,1-b]furan can be carried out in a manner known per se, especially by acid-catalyzed cyclization of the reduction product at low temperatures in an inert organic solvent. Suitable reaction conditions are given, for example, in Japanese Patent Publication (Kokai) No. 258,773/1190 using about 1 to 5 mol or chlorosulphonic acid as the acid catalyst per 1 mol of starting material and a nitroalkane, aliphatic halogenated hydrocarbon or aliphatic ether or a mixture of two or more of these solvents at temperature between about −100° C. and 0° C., preferably −80° C. and −30° C., with subsequent treatment of the reaction mixture with excess water; see especially Example 9) and in European Patent Publication No. 403 945 (using diverse types of acidic catalysts and solvents at temperatures from about −60° C. to about 30° C.; see especially page 4, line 48 to page 5 line 16 and Example 1).

The following Examples serve to illustrate the invention in more detail. The abbreviation GC stands for gas chromatography. Unless otherwise indicated "room temperature" means about 25° C.

EXAMPLE 1

A solution of 10 g (43.1 mmol) of E,E-6-(2',6',6'-trimethylcyclohex-1'-en-1'-yl)-4-methyl-hexa-1,4-dien-1-al in 30 ml of tetrahydrofuran was added dropwise to a solution of 0.98 g (25.86 mmol) of lithium aluminum hydride in 45 ml of tetrahydrofuran at room temperature. The resulting reaction was slightly exothermic. The mixture was heated at reflux temperature for about 18¼ hours while stirring. Subsequently, the mixture was cooled to 10° C., treated with ice-water and its pH value was adjusted to 4 by the addition of 2N sulphuric acid. The aqueous phase was then extracted with diethyl ether and the organic phase was washed in sequence with water, saturated sodium bicarbonate solution and saturated sodium chloride solution. The combined organic solutions were dried over anhydrous magnesium sulphate and concentrated under reduced pressure. Finally, the resulting crude product was dried in a high vacuum. In this manner there were obtained 10.07 g (99% of the theoretical yield) of a mixture of E-and Z-6-(2',6',6'-trimethyl-cyclohex-1'-en-1'-yl)-4-methyl-hex-3-en-1-ol (E: 23%; Z: 59%; in each case GC area percent) as well as E-or Z-6-(2',6',6'-trimethyl-cyclohex-1'-en-1'yl)-4-methyl-hex-4-en-1-ol (17% GC area percent).

Mass spectrum (m/e): E-6-(2',6',6'-Trimethyl-cyclohex-1'-en-1'-yl)-4-methyl-hex-3-en-1-ol: 236 (9.5), 138 (11.7), 137 (100), 136 (14.4), 121 (8.5), 107 (7.9), 95 (56.3), 93 (9.3), 81 (39.8), 79 (9.2), 69 (16.2), 67 (11.2), 57 (7.4), 55 (16.3), 53 (8.5), 43 (9.0), 41 (27.5), 31 (6.6);

Z-6-(2',6',6'-Trimethyl-cyclohex-1'-en-1'-yl)-4-methyl-hex-3-en-1-ol: 236 (4.4), 138 (11.0), 137 (100), 136 (12.1), 121 (6.6), 107 (8.1), 95 (60.5), 93 (9.3), 91 (7.2), 81 (43.8), 79 (9.3), 69 (17.8), 67 (13.3), 57 (10.2), 55 (19.5), 53 (8.8), 43 (10.9), 41 (33.3), 31 (7.2), 29 (6.9);

E- or Z-(probably E-) 6-(2',6',6'-Trimethyl-cyclohex-1'-en-1'-yl)-4-methyl-hex-4-en-1-ol: 236 (28.7), 221 (8.2), 177 (13.8), 149 (5.9), 137 (100.0), 136 (25.6), 123 (31.6), 121 (40.2), 109 (16.0), 107 (29.8), 95 (72.9), 93 (29.3), 91 (17.9), 85 (17.0), 81 (58.9), 79 (21.5), 69 (32.1), 67 (22.9), 55 (35.4), 43 (21.8), 41 (53.2).

EXAMPLE 2

A mixture of 0.8 g (2 mmol) of tricaprylmethylammonium chloride (Aliquat 336 from Fluka), 9.93 g (118.2 mmol) of sodium carbonate and 10.29 g (59.11 mmol) of sodium dithionite was placed in 65 ml of water. A solution of 1.53 g (6.59 mmol) of 6-(2',6',6'-trimethyl-cyclohex-1'-en-1'-yl)-4-methyl-hexa-2,4-dien-1-al in 65 ml of toluene was added dropwise to this mixture at room temperature within 15 minutes. The reaction mixture was heated to reflux temperature and after 22 hours a further 2.29 g (13 mmol) of sodium dithionite and 2.21 g of sodium carbonate are added thereto. After heating at reflux temperature for a further 46.5 hours the mixture was cooled to room temperature, extracted with diethyl ether and the organic phase was washed in sequence with 0.5N hydrochloric acid, saturated sodium bicarbonate solution and saturated sodium chloride solution, dried over anhydrous magnesium sulphate and evaporated under reduced pressure. The crude product (2.37 g) was distilled in a bulb tube. In this manner there were obtained 1.5 g of a product which, according to gas chromatography, consisted of E- or Z-6-(2',6',6'-trimethylcyclohex-1'-en-1'-yl)-4-methyl-hex-4-en-1-ol (30% GC area percent), Z-6-(2',6',6'-trimethyl-cyclohex-1'-en-1'-yl)-4-methyl-hex-3-en-1-ol (15% GC area percent), E-6-(2',6',6'-trimethyl-cyclohex-1'-en-1'-yl)-4-methyl-hex-3-en-1-ol (32% GC area percent) as well as an unknown compound (17% GC area percent).

The distilled product was eluted over 200 g of silica gel 60 (Merck; 0.04 bis 0.06 mm) using 5% to 30% diethyl ether in n-hexane as the eluent. In this manner there was obtained 0.21 g of a 1:1 mixture of 6-(2',6',6'-trimethyl-cyclohex-1'-en-1'-yl)-4-methyl-hexanal and presumably 6-(2',6',6'-trimethyl-cyclohex-1'-en-1'-yl)-4-methyl-hex-4-en-1-al (the latter compound could not be obtained in pure form) as well as 0.87 g of a mixture which, according to gas chromatography, consisted of E- or Z-6-(2',6',6'-trimethyl-cyclohex-1'-en-1'-yl)-4- methyl-hex-4-en-1-ol (38% GC area percent), Z-6-(2',6',6'-trimethyl-cyclohex-1'-en-1'-yl)-4-methyl-hex-3-en-1-ol (19% GC area percent) as well as E-6-(2',6',6'-trimethyl-cyclohex-1'-en-1'-yl)-4-methyl-hex-3-en-1-ol (41% GC area percent).

Physical data: 6-(2',6',6'-Trimethyl-cyclohex-1'-en-1'-yl)-4-methyl-hexanal:

H-NMR (200 MHz,CDCl$_3$) 0.94 ppm (d,J=6,3H), 0.98 ppm (s,6H), 1.57 ppm (s,3H), 9.78 ppm (dd,J=2,J=2,1H); $^{13}$C-NMR: 19.25 ppm (q), 19.58 ppm (t), 19.81 ppm (q), 26.26 ppm (t), 28.66 ppm (q), 28.83 ppm (t), 32.77 ppm (t), 33.61 ppm (d), 34.95 ppm (s), 37.19 ppm (t), 39.90 ppm (t), 41.79 ppm (t), 126.64 ppm (s), 137.42 ppm (s), 202.74 ppm (d);

Mass spectrum (m/e):

236(11.3), 221 (23.1), 137 (7.0), 124 (12.6), 123 (100), 127 (7.0), 109 (13.2), 107 (8.4), 95 (28.5), 93 (8.4), 81 (33.3), 79 (7.3), 69 (11.6), 67 (13.4), 55 (16.8), 43 (9.2), 41 (18.3), 29 (7.5).

This compound can also be produced readily and in good yield by hydrogenating compound II in the presence of palladium on charcoal in ethanol.

EXAMPLE 3

6.72 g (177 mmol) of sodium borohydride were placed in 750 ml of isopropanol at room temperature. A solution of 150 g (0.65 mol) of 6-(2',6',6'-trimethyl-cyclohex-1'-en-1'-yl)-4-methyl-hexa-2,4-dien-1-al in 750 ml of isopropanol was added dropwise thereto while stirring. After the addition of a fifth of this solution the internal temperature of the reaction mixture had risen from 26° C. to 30° C. and the solution was therefore cooled to 20° C. with an ice/water bath. The addition was complete after 1¼ hours. The mixture was stirred at room temperature for a further 3 hours, then poured on to ice and the aqueous mixture was diluted with diethyl ether. 25 ml of 2N hydrochloric acid were added dropwise to the mixture while stirring constantly. After stirring for 30 minutes the mixture was neutralized with saturated sodium bicarbonate solution and the organic phase was separated and concentrated under reduced pressure. The residue was then diluted with diethyl ether and the solution was dried with anhydrous magnesium sulphate and concentrated under reduced pressure. In this manner there were obtained 135 g (89% of the theoretical yield) of 6-(2',6',6'-trimethyl-cyclohex-1'-en-1'-yl)-4-methyl-hexa-2,4-dien-1-ol.

Physical data:

6-(2',6',6'-Trimethyl-cyclohex-1'-en-1'-yl)-4-methyl-hexa-2,4-dien-1-ol:

H-NMR (200 MHz, CDCl$_3$) 0.96 ppm (s,3H), 1.53 ppm (s,3H), 1.8 ppm (d,J=1 Hz,3H), 2.83 ppm (d,J=7 Hz,2H), 4.18 ppm (d,J=7 Hz,2H), 5.35 ppm (dd,J=7 Hz,J=7 Hz,1H), 5.7 ppm (ddd,J=7 Hz,J=7 Hz,J=15 Hz,1H), 6.25 ppm (d,J=15 Hz,1H);

C$^{13}$-NMR (CDCl$_3$): 12.26 ppm (q), 19.38 ppm (t), 19.54 ppm (q), 27.43 ppm (t), 28.12 ppm (q), 32.72 ppm (t), 34.73 ppm (s), 39.61 ppm (t), 63.42 ppm (t), 124.59 ppm (d), 127.86 ppm (s), 131.25 ppm (s), 134.20 ppm (d), 135.99 ppm (s), 136.41 ppm (d);

Mass spectrum (m/e):

234 (22.0), 203 (21.9), 145 (30.2), 133 (48.3), 123 (57.8), 119 (85.7), 110 (39.8), 105 (78.0), 95 (52.3), 93 (82.6), 91 (56.1), 81 (95.0), 77 (37.5), 69 (59.2), 67 (41.1), 55 (80.9), 43 (53.4), 41 (100).

EXAMPLE 4

2 g (8.62 mmol) of 6-(2',6',6'-trimethyl-cyclohex-1'-en-1'-yl)-4-methyl-hexa-2,4-dien-1-al are placed in 10 of toluene at room temperature. 2 ml of a 70% solution of sodium bis(2-methoxyethoxy)aluminium dihydride (7 mmol) in toluene were added to the mixture and the reaction mixture was heated to 90° C. while stirring. After stirring at 105° C. for 8 hours the mixture was cooled, poured into water and diluted with diethyl ether. The separated organic phase was washed with 2N hydrochloric acid and subsequently with saturated sodium bicarbonate, dried over anhydrous magnesium sulphate and concentrated under reduced pressure. In this manner there were obtained 1.89 g (93.6% of the theoretical yield) of 6-(2',6',6'-trimethyl-cyclohex-1'-en-1'-yl)-4-methyl-hexa-2,4-dien-1-ol.

EXAMPLE 5

0.98 g (25.86 mmol) of lithium aluminum hydride was placed in 45 ml of diethyl ether at room temperature and a solution of 10 g (43.1 mmol) of 6-(2',6',6'-trimethyl-cyclohex-1'-en-1'-yl)-4-methyl-hexa-2,4-dien-1-al in 40 ml of diethyl ether was added dropwise within 10 minutes. The reaction mixture was stirred at reflux temperature for 22¼ hours. Then, it was cooled to 8° C., treated dropwise with ice-water and adjusted to pH 2 with 2N sulphuric acid. The separated aqueous phase was extracted with diethyl ether, the organic phase was washed in sequence with water, saturated sodium bicarbonate solution and saturated sodium chloride solution (to neutrality), dried with anhydrous magnesium sulphate and concentrated under reduced pressure. In this manner there were obtained 10.04 g (99% of the theoretical yield) of 6-(2',6',6'-trimethyl-cyclohex-1'-en-1'-yl)-4-methyl-hexa-2,4-dien-1-ol.

EXAMPLE 6

A solution of 2 g (9 mmol) of 6-(2',6',6'-trimethyl-cyclohex-1'-en-1'-yl)-4-methyl-hexa-2,4-dien-1-ol (produced according to the process described in Example 3, 4 or 5) in 5 ml of tetrahydrofuran was added dropwise at room temperature to a solution of 0.32 g (8.45 mmol) of lithium aluminium hydride in 24 ml of tetrahydrofuran. The reaction mixture was then heated to reflux temperature and, after 24 hours, treated cautiously with ice-water. The mixture was poured into a mixture of diethyl ether and ice-water, adjusted to pH 4 with sulphuric acid and extracted with diethyl ether. The separated organic phase was washed in sequence with saturated sodium bicarbonate solution and saturated sodium chloride solution, dried over anhydrous magnesium sulphate and evaporated under reduced pressure. In this manner there were obtained 1.8 g of a mixture of E- or Z-6-(2',6',6'-trimethyl-cyclohex-1'-en-1'-yl)-4-methyl-hex-4-en-1-ol (20% GC area percent), Z-6-(2',6',6'-trimethyl-cyclohex-1'en-1'-yl)-4-methyl-hex-3-en-1-ol (39% GC area percent) as well as E-6-(2',6',6'-trimethyl-cyclohex-1'-en-1'-yl)-4-methyl-hex-3-en-1-ol (33% GC area percent).

EXAMPLE 7

2 g (9 mmol) of 6-(2',6',6'-trimethyl-cyclohex-1'-en-1'-yl)-4-methyl-hexa-2,4-dien-1-ol (produced according to the process described in Example 3, 4 or 5) were added at room temperature to a mixture of 2.6 g (30 mmol) of sodium bicarbonate and 0.97 g (3 mmol) of tetrabutylammonium bromide in 5 ml of water and 6 ml of tetrahydrofuran and the reaction mixture was heated to reflux temperature. Then, a solution of 1.3 g (15 mmol) of sodium bicarbonate and 3.3 g (19 mmol) of sodium dithionite in 20 ml of water was added dropwise within 30 minutes. The reaction mixture was heated at reflux temperature for 21 hours and subsequently the same amount of the aforementioned solution was added thereto. A further double amount of the aforementioned solution was also added after stirring for a further 26 hours. The mixture was heated at reflux temperature for a further 43 hours, subsequently cooled, extracted with diethyl ether and the separated organic phase was washed with saturated sodium chloride solution, dried over anhydrous magnesium sulphate and concentrated under reduced pressure. In this manner there were obtained 1.5 g of a mixture of E- and Z-6-(2',6',6'-trimethyl-cyclohex-1'-en-1'-yl)-4-methyl-hex-3-en-1-ol (E: 31%; Z: 29%; in each case GC area percent) as well as unreacted starting material 6-(2',6',6'-trimethyl-cyclohex-1'-en-1'-yl)-4-methyl-hexa-2,4-dien-1-ol (31% GC area percent).

EXAMPLE 8

50 g (429 mmol) of chlorosulphonic acid were added dropwise while stirring to 25 ml of 2-nitropropane cooled to −69° C. Then, a solution, pre-cooled to −65° C., of 10 g (42.37 mmol) of the mixture of E- and Z-6-(2',6',6'-trimethyl-cyclohex-1'-en-1'-yl)-4-methyl-hex-3-en-1-ol (E: 23%; Z: 59%) and E- or Z-6-(2',6',6'-trimethylcyclohex-1'-en-1'-yl)-4-methyl-hex-4-en-1-ol (17%) in 100 ml of methylene chloride was added dropwise within 40 minutes. The reaction mixture was stirred at −71° C. for 1¼ hours, then neutralized with 120 ml of triethylamine while cooling, whereby the dropwise addition took 2 hours. The resulting precipitated salt was filtered off under suction and washed with n-hexane. The combined organic phases (including n-hexane rinsings) were washed with saturated sodium bicarbonate solution, dried over anhydrous magnesium sulphate and concentrated under reduced pressure. The residue (6.35 g) was distilled in a bulb tube and there were obtained in this manner 5.25 g (52.5% of the theoretical yield) of a mixture of (±)-[3aα,5aβ,9aα,9bβ]-dodecahydro-3a,6,6,9a-tetramethylnaphtho[2,1-b]furan [(±)-AMBROX ®; 30% area percent according to gas chromatography] and (±)-[3aα,5aβ,9aα,9bα]-dodecahydro-3a,6,6,9a-tetramethylnaphtho[2,1-b]furan[(±)-epiambrox; 61% area percent according to gas chromatography].

I claim:

1. A process for the manufacture of 6-(2',6',6'-trimethyl-cyclohex-1'-en-1'-yl)-4-methyl-hex-3-en-1-ol, -4-en-1-ol, or mixtures thereof, having the formula

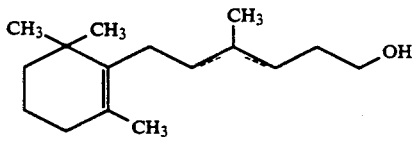

wherein one of the bonds ========= denotes a single bond and the other denotes a double bond, said process comprising an initial reducing step in which E,E-6-(2',6',6'-trimethyl-cyclohex-1'-en-1'-yl)-4-methyl-hexa-2,4-dien-1-al is reduced using a reducing agent which is selected from the group consisting of (a) lithium aluminium hydride, (b) sodium dithionite in the presence of sodium bicarbonate in aqueous solution and of a phase transfer catalyst, (c) sodium borohydride, and (d) sodium bis(2-methoxyethoxy)aluminium dihydride.

2. The process according to claim 1, wherein the reducing agent which is used in said initial reducing step is selected from the group consisting of reducing agents (a), (c) or (d), and wherein E,E-6-(2',6',6'-trimethyl-cyclohex-1'-en-1'-yl)-4-methyl-hexa-2,4-dien-1-ol, having the formula

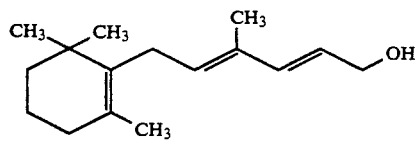

in E, E-form results as an intermediate, said process further comprising a second reducing step wherein the intermediate of formula III is reduced further to the desired 6-(2',6',6'-trimethyl-cyclohex-1'-en-1'-yl)-4-methyl-hex-3-en-1-ol, -4-en-1-ol, or mixture thereof using reducing agents (a) or (b).

3. The process according to claim 1, further comprising converting the compound of formula I into a mixture of [3aα,5aβ,9aα,9bβ]-dodecahydro-3a,6,6,9a-tetramethylnaphtho[2,1-b]furan and [3aα,5aβ,9aα,9bα]-dodecahydro-3a,6,6,9a-tetramethylnaphtho[2,1-b]furan.

4. The process according to claim 1, wherein the E,E-6-(2',6',6'-trimethyl-cyclohex-1'-en-1'-yl)-4-methyl-hexa-2,4-dien-1-al is heated with lithium aluminium hydride in an ethereal solvent at temperatures between about 65° C. and about 165° C., whereby the compounds of formula I are obtained.

5. The process according to claim 2, wherein the E,E-6-(2',6',6'-trimethyl-cyclohex-1'-en-1'-yl)-4-methyl-hexa-2,4-dien-1-al is held at or warmed to temperatures of about room temperature to about 40° C. with lithium aluminium hydride in an aliphatic ether during the initial reducing step, whereby the compound of formula III is obtained.

6. The process according to claim 1, wherein, during the initial reducing step, the E,E-6-(2',6',6'-trimethyl-cyclohex-1'-en-1'-yl)-4-methyl-hexa-2,4-dien-1-al is heated with sodium dithionite in the presence of sodium bicarbonate in aqueous solution, an aliphatic ether, an aromatic hydrocarbon or a lower aliphatic ester as an additional solvent and of a quaternary ammonium salt or of a phosphonium salt as the phase transfer catalyst at the reflux temperature of the reaction mixture, whereby the compounds of formula I are obtained.

7. The process according to claim 2, wherein, during the initial reducing step, the E,E-6-(2', 6',6'-trimethyl-cyclohex-1'-en-1'-yl)-4-methyl-hexa-2,4-dien-1-al is heated with sodium borohydride in an alcohol or aqueous alcohol at the reflux temperature of the reaction mixture, whereby the compound of formula III is obtained.

8. The process according to claim 2, wherein, during the initial reducing step, the E,E-6-(2',6',6'-trimethyl-cyclohex-1'-en-1'-yl)-4-methyl-hexa-2,4-dien-1-al is heated with sodium bis(2-methoxyethoxy)aluminium dihydride in an aromatic hydrocarbon or a cyclic ether at the reflux temperature of the reaction mixture, whereby the compound of formula III is obtained.

* * * * *